(12) United States Patent
Haremza et al.

(10) Patent No.: US 9,034,955 B2
(45) Date of Patent: May 19, 2015

(54) HIGH MOLECULAR WEIGHT NONPOLAR BENZOTRIAZOLES

(75) Inventors: Sylke Haremza, Neckargemuend (DE); Andrea Misske, Speyer (DE); Simon Schambony, Ludwigshafen (DE); Alban Glaser, Mannheim (DE)

(73) Assignee: BASF SE, Ludwigshafen (DE)

( * ) Notice: Subject to any disclaimer, the term of this patent is extended or adjusted under 35 U.S.C. 154(b) by 800 days.

(21) Appl. No.: 13/266,609

(22) PCT Filed: May 11, 2010

(86) PCT No.: PCT/EP2010/056489
§ 371 (c)(1),
(2), (4) Date: Oct. 27, 2011

(87) PCT Pub. No.: WO2010/130752
PCT Pub. Date: Nov. 18, 2010

(65) Prior Publication Data
US 2012/0059095 A1  Mar. 8, 2012

(30) Foreign Application Priority Data
May 15, 2009  (EP) ..................... 09160348

(51) Int. Cl.
| C08K 5/00 | (2006.01) |
| C08F 8/00 | (2006.01) |
| C07D 293/00 | (2006.01) |
| C08K 5/3475 | (2006.01) |
| C07D 249/20 | (2006.01) |
| C07D 401/14 | (2006.01) |

(52) U.S. Cl.
CPC ............... C08K 5/3475 (2013.01); C08F 8/00 (2013.01); C07D 249/20 (2013.01); C07D 401/14 (2013.01)

(58) Field of Classification Search
CPC .. C08K 5/3475; C08K 5/3435; C07D 249/20; C08F 8/00
USPC ................ 524/91; 525/55; 548/260
See application file for complete search history.

(56) References Cited

U.S. PATENT DOCUMENTS

| 3,213,058 A | 10/1965 | Boyle et al. |
| 4,853,471 A * | 8/1989 | Rody et al. ............. 548/261 |
| 4,973,702 A | 11/1990 | Rody et al. |
| 5,032,498 A | 7/1991 | Rody et al. |
| 5,523,379 A | 6/1996 | Rosenquist |
| 5,807,963 A | 9/1998 | Rosenquist |
| 2004/0209981 A1 | 10/2004 | Lazzari et al. |
| 2007/0095432 A1 | 5/2007 | Musa |
| 2007/0277907 A1 | 12/2007 | Musa |
| 2010/0184887 A1 | 7/2010 | Gonzalez et al. |
| 2010/0267893 A1 | 10/2010 | Schambony et al. |
| 2011/0130273 A1 | 6/2011 | Karpov et al. |
| 2011/0237665 A1 | 9/2011 | Misske et al. |

FOREIGN PATENT DOCUMENTS

| DE | 38 36 630 | 5/1989 |
| EP | 0 057 160 | 8/1982 |
| EP | 0 214 102 | 3/1987 |
| EP | 0 280 650 | 8/1988 |
| EP | 0 718 341 | 6/1996 |
| EP | 1 191 041 | 3/2002 |
| JP | 60 124635 | 7/1985 |
| JP | 63-205334 A | 8/1988 |
| JP | 05-117444 A | 5/1993 |
| WO | 98 25922 | 6/1998 |
| WO | 03 004490 | 1/2003 |

OTHER PUBLICATIONS

International Search Report Issued Dec. 3, 2010 in PCT/EP10/056489 Filed May 11, 2010.
U.S. Appl. No. 61/119,556, filed Dec. 3, 2008, Misske, et al.
U.S. Appl. No. 61/160,124, filed Mar. 13, 2009, Misske, et al.
U.S. Appl. No. 13/254,936, filed Sep. 6, 2011, Misske, et al.

* cited by examiner

*Primary Examiner* — Susannah Chung
*Assistant Examiner* — Atnaf Admasu
(74) *Attorney, Agent, or Firm* — Oblon, McClelland, Maier & Neustadt, L.L.P.

(57) ABSTRACT

The present invention relates to the use of certain benzotriazole derivatives of the general formula (I)

$$[B\text{---}]_n A \quad (I)$$

where
B is an optionally substituted 2-(2-hydroxyphenyl)-2H-benzotriazole group,
n is an integer from the range from 3 to 20 and
A is an n-valent organic radical,
as UV absorber or stabilizer in inanimate organic materials. Furthermore, the invention relates to methods of stabilizing inanimate organic materials, in particular plastics, against the effect of light using specific benzotriazole derivatives. Further subject matters of the invention are certain benzotriazole derivatives and inanimate organic materials comprising certain benzotriazole derivatives.

20 Claims, No Drawings

HIGH MOLECULAR WEIGHT NONPOLAR BENZOTRIAZOLES

The present invention relates to the use of certain benzotriazole derivatives as UV absorbers and for stabilizing inanimate organic materials. Furthermore, the invention relates to methods of stabilizing inanimate organic materials, in particular plastics, against the effect of light using specific benzotriazole derivatives. Further subject matters of the invention are certain benzotriazole derivatives and inanimate organic materials comprising certain benzotriazole derivatives.

Further embodiments of the present invention can be found in the claims, the description and the examples. It goes without saying that the features of the subject matter according to the invention specified above and still to be explained below can be used not only in the combination specifically cited in each case, but also in other combinations, without departing from the context of the invention. Preferred or very preferred embodiments of the present invention are in particular also those in which all of the features of the subject matter according to the invention have the preferred or very preferred meanings.

Benzotriazole derivatives are known to the person skilled in the art from the prior art generally as photostabilizers or UV absorbers, for example for applications in plastics, coatings, inks or in cosmetics. These benzotriazole derivatives, however, are often low molecular weight compounds with a molecular weight of significantly below 1000 g/mol.

EP 0 280 650 A1 describes the use of certain benzotriazole derivatives as photoprotective agents for recording materials for inkjet printing. The relatively high molecular weight benzotriazoles described in this specification can comprise a plurality of benzotriazole groups and thereby achieve molecular weights which can exceed 1000 g/mol. These relatively high molecular weight benzotriazoles are characterized by increased hydrophilicity and dispersibility in oil-in-water emulsions and are therefore used according to the teaching of EP 0 280 650 A1 for aqueous systems and inks.

EP 0 057 160 A1 describes 2-(2-hydroxyphenyl)benzotriazoles, their use as UV absorbers and their preparation. The UV absorbers are used in particular for stabilizing coatings and photomaterial. Only derivatives with one or two benzotriazole groups and a molecular mass of generally less than 1000 g/mol are described.

U.S. Pat. No. 3,213,058 describes o-hydroxyphenylbenzotriazoles comprising a benzotriazole group, their use as UV absorbers in plastics and plastics comprising these o-hydroxyphenylbenzotriazoles. Furthermore, U.S. Pat. No. 3,213,058 describes polymers modified with these o-hydroxyphenylbenzotriazoles, namely resins based on esters of o-hydroxyphenylbenzotriazoles with hydroxyl-containing or carboxyl-containing copolymerized monomers.

Photostabilizers and UV absorbers based on the aforementioned low molecular weight benzotriazole derivatives are therefore known from the prior art.

During the finishing of inanimate organic materials, in particular plastics (polymers), with UV absorbers or stabilizers, the problem often arises that the UV absorbers or stabilizers leave the polymer matrix over the course of time, for example by migrating to the surface of the polymer (migration). This is particularly critical if, as a result of the migration, UV absorbers or stabilizers come into contact with foods by, for example, passing from the packaging material to the packaged article.

Furthermore, there is therefore the need to increase the stability (service life) of UV absorbers or stabilizers in inanimate organic materials.

The lack of compatibility of the UV absorbers or stabilizers with inanimate organic materials, for example polyolefins or other plastics, and the thermal decomposition of the stabilizers upon incorporation into polymers at elevated temperature is often also unsatisfactory.

It was therefore an object of the invention to provide UV absorbers or stabilizers which lead to a further suppression of the migration from inanimate organic material. Furthermore, these UV absorbers or stabilizers should bring with them improvements in the life of the stabilization of inanimate organic material. It was a further part object of the invention to provide UV absorbers or stabilizers which have good compatibility with the materials to be stabilized, for example polyolefins and other plastics, and stability upon incorporation into the material to be stabilized.

As is evident from the disclosure of the present invention, these and other objects are achieved by the various embodiments of the use according to the invention of benzotriazole derivatives of the general formula (I)

 (I)

where
- B is an optionally substituted 2-(2-hydroxyphenyl)-2H-benzotriazole group,
- n is an integer from the range from 3 to 20 and
- A is an n-valent organic radical, as UV absorber or stabilizer in inanimate organic materials.

Mixtures of benzotriazole derivatives of the general formula (I) are of course also suitable as UV absorber or stabilizer in inanimate organic materials.

Within the context of this invention, expressions of the form $C_a$-$C_b$ refer to chemical compounds or substituents with a specific number of carbon atoms. The number of carbon atoms can be selected from the entire range from a to b, including a and b, a is at least 1 and b is always greater than a. Further specification of the chemical compounds or substituents takes place through expressions of the form $C_a$-$C_b$—V. V here is a chemical compound class or substituent class, for example alkyl compounds or alkyl substituents.

Halogen is fluorine, chlorine, bromine or iodine, preferably fluorine, chlorine or bromine, particularly preferably chlorine.

Specifically, the collective terms given for the various substituents have the following meaning:

$C_1$-$C_{20}$-alkyl: straight-chain or branched hydrocarbon radicals having up to 20 carbon atoms, for example $C_1$-$C_{10}$-alkyl or $C_{11}$-$C_{20}$-alkyl, preferably $C_1$-$C_{10}$-alkyl, for example $C_1$-$C_3$-alkyl, such as methyl, ethyl, propyl, isopropyl, or $C_4$-$C_6$-alkyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, or $C_7$-$C_{10}$-alkyl, such as heptyl, octyl, 2-ethylhexyl, 2,4,4-trimethylpentyl, 1,1,3,3-tetramethylbutyl, nonyl or decyl, and isomers thereof.

Aryl: a mono- to trinuclear aromatic ring system comprising 6 to 14 carbon ring members, e.g. phenyl, naphthyl or anthracenyl, preferably a mono- to dinuclear, particular preferably a mononuclear, aromatic ring system.

Arylalkyl is a mono- to trinuclear aromatic ring system (as mentioned above) which is attached via a $C_1$-$C_{20}$-alkylene group, preferably a $C_1$-$C_{14}$-alkylene group, preferably a mono- to dinuclear, particularly preferably a mononuclear, aromatic ring system.

$C_1$-$C_{20}$-alkylene: straight-chain or branched hydrocarbon radicals having 1 to 20 carbon atoms, for example $C_1$-$C_{10}$-alkylene or $C_{11}$-$C_{20}$-alkylene, preferably $C_1$-$C_{10}$-alkylene, in particular methylene, dimethylene, trimethylene, tetramethylene, pentamethylene or hexamethylene.

$C_1$-$C_{20}$-alkoxy is a straight-chain or branched alkyl group having 1 to 20 carbon atoms (as specified above), which are bonded via an oxygen atom (—O—), for example $C_1$-$C_{10}$-alkoxy or $C_1$-$C_{20}$-alkoxy, preferably $C_1$-$C_{10}$-alkyloxy, particularly preferably $C_1$-$C_3$-alkoxy, such as, for example, methoxy, ethoxy, propoxy.

$C_3$-$C_{15}$-cycloalkyl: monocyclic, saturated hydrocarbon groups having 3 to 15 carbon ring members, preferably $C_3$-$C_8$-cycloalkyl such as cyclopropyl, cyclobutyl, cyclopentyl, cyclohexyl, cycloheptyl or cyclooctyl and a saturated or unsaturated polycyclic system such as, for example, norbornyl or norbenyl. Particular preference is given to $C_5$-$C_6$-cycloalkyl.

Heteroatoms are phosphorus, oxygen, nitrogen or sulfur, preferably oxygen, nitrogen or sulfur, whose free valences are optionally saturated by H atoms.

UV absorbers absorb UV light with a wavelength of less than 400 nm, in particular from 200 to 400 nm. UV absorbers can therefore absorb, for example, UV-A (from 320 to 400 nm), UV-B (from 290 to 319 nm) and/or UV-C (from 200 to 289 nm) light. Preferably, UV absorbers absorb UV-A and/or UV-B light. Very particularly preferably UV absorbers absorb UV-A and/or UV-B light and deactivate the absorbed light energy in a nonradiative manner.

In one preferred embodiment of the invention, as benzotriazole derivatives, those of the general formula (Ia)

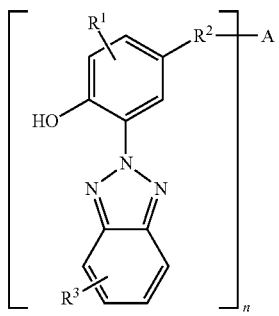

(Ia)

where
n is an integer from the range from 3 to 20,
$R^1$ is H, $C_1$-$C_{20}$-alkyl, arylalkyl, $C_5$-$C_{20}$-alkoxycarbonylalkyl, $C_3$-$C_{15}$-cycloalkyl,
$R^3$ is H, halogen, $CF_3$, $COOR^4$,
$R^4$ is H, $C_1$-$C_{20}$-alkyl,
$R^2$ is a single bond, O, $NR^7$
   or a group of the general formula (IIa)

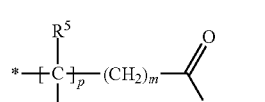

(IIa)

(*bonding to benzotriazole   **bonding to A)

m is an integer from the range from 0 to 4,
p is 0 or 1,
A is an n-valent organic radical,
$R^5$ is H, $C_1$-$C_{20}$-alkyl,
$R^6$ is H, $C_1$-$C_{20}$-alkyl,
X is O, $NR^7$,
$R^7$ is H, $C_1$-$C_{20}$-alkyl,
are used as UV absorbers or stabilizers in inanimate organic materials. Here, in formula (Ia), n is very preferably an integer from the range from 3 to 10, in particular from 3 to 6. Here, $R^3$ is very preferably H or Cl, in particular $R^3$ is fixed at the 3-position of the benzotriazole group. Here, in formula (IIa), m is very preferably an integer from the range from 1 to 3, particularly preferably 1 or 2, in particular 2. Very preferably here, p=0, likewise very preferably here p=1. $R^7$ is preferably H.

In a further preferred embodiment of the invention, as benzotriazole derivatives, those of the general formula (Ib)

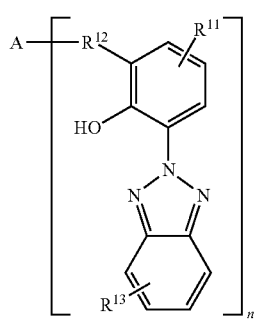

(Ib)

where
$R^{11}$ is H, $C_1$-$C_{20}$-alkyl, arylalkyl, $C_5$-$C_{20}$-alkoxycarbonylalkyl, $C_3$-$C_{15}$-cycloalkyl,
$R^{13}$ is H, halogen, $CF_3$, $COOR^{14}$,
$R^{14}$ is H, $C_1$-$C_{20}$-alkyl,
$R^{12}$ is a single bond, O, $NR^7$
   or a group of the general formula (IIa)
are used as UV absorbers or stabilizers in inanimate organic materials, the remaining substituents and indices having the meanings given above for (Ia). Here, in formula (Ib), n is very preferably an integer from the range from 3 to 10, in particular from 3 to 6. Here, $R^{13}$ is very preferably H or Cl, in particular $R^{13}$ is fixed at the 3-position of the benzotriazole group. Here, in formula (IIa), m is very preferably an integer from the range from 1 to 3, particularly preferably 1 or 2, in particular 2. Very preferably here p=0, likewise very preferably here p=1.

In one preferred embodiment of the invention, as benzotriazole derivatives, those of the general formula (Ic)

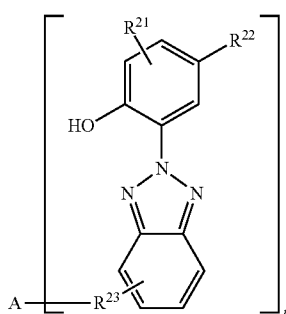

(Ic)

where $R^{21}$ is H, $C_1$-$C_{20}$-alkyl, arylalkyl, $C_5$-$C_{20}$-alkoxycarbonylalkyl, $C_3$-$C_{15}$-cycloalkyl, $R^{22}$ is H, $C_1$-$C_{20}$-alkyl, $COOR^{24}$, $R^{24}$ is H, $C_1$-$C_{20}$-alkyl, $R^{23}$ is a single bond, O, $NR^7$ or a group of the general formula (IIa)

are used as UV absorbers or stabilizers in inanimate organic materials, the remaining substituents and indices having the meanings given above for (Ia). Here, in formula (Ic), n is very preferably an integer from the range from 3 to 10, in particular from 3 to 6. Here, $R^{22}$ is very preferably $C_1$-$C_{20}$-alkyl. Here, in formula (IIa), m is very preferably an integer from the range from 1 to 3, particularly preferably 1 or 2, in particular 2. Very preferred here is p=0, likewise very preferred here is p=1.

Methods of preparing benzotriazole derivatives are known to the person skilled in the art. The benzotriazole ring can generally be prepared from the corresponding aminophenyl and phenol by a sequence of diazotization, coupling and reduction, as described, for example, in EP 0214102. The further derivatization of the benzotriazoles and/or phenol rings is described, for example, in EP 57160.

The molecular weight (number-average Mn) of the benzotriazole derivatives of the general formulae (I), (Ia), (Ib) or (Ic) is preferably from 1100 g/mol to 5000 g/mol, particularly preferably from 1500 to 5000 g/mol, in particular from 2000 to 5000 g/mol.

The n-valent organic radicals A are generally based on organic compounds which are reacted with a number n of benzotriazole derivatives comprising, for example, the benzotriazole substituents of the formulae (Ia)-(Ic). For example, the n-valent organic radicals are linear or branched hydrocarbon radicals which may in each case be optionally interrupted in any desired position by one or more heteroatoms. For example, suitable organic compounds on which the n-valent organic radicals are based are polyols, polyesterpolyols, polyetherpolyols, polyetheramines and epoxide compounds, polymers comprising maleic acid groups or derivatives of maleic acid groups, polycarboxylic acids, cyanuric acid or cyanuric chloride derivatives, in particular ethoxylated or propoxylated polyols. Preference is given here to polymers comprising maleic acid groups or derivatives of maleic acid groups, polyols, in particular ethoxylated or propoxylated polyols or polyetheramines.

Suitable polyetheramines comprise, for example, triaminopolyalkylene oxide compounds. This is to be understood as meaning that these compounds on the one hand comprise three amino functions (NH or $NH_2$ functions), and on the other hand comprise alkylene oxide building blocks. The last-mentioned building blocks are in particular ethylene oxide and/or propylene oxide and/or butylene oxide.

The polyetheramines can be used individually or in the form of mixtures.

In a further embodiment, reaction products of the polyols with propylene oxide and/or ethylene oxide are used, with preferably 1 to 5 mol of propylene oxide and/or ethylene oxide being used per mol of polyol.

In a preferred embodiment of the invention, those benzotriazole derivatives are used in which the group A corresponds to an n-valent organic radical of the general formula (III)

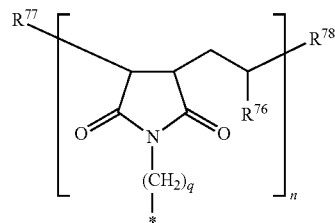

(III)

where n is an integer from the range from 3 to 20, q is an integer from the range from 0 to 10, $R^{76}$ is H, aryl, $C_1$-$C_{30}$-alkyl, $R^{77}$ is H, $C_1$-$C_{20}$-alkyl, $C_1$-$C_{20}$-alkoxy, $R^{78}$ is H, $C_1$-$C_{20}$-alkyl, $C_1$-$C_{20}$-alkoxy, where * designates the bonding of the benzotriazole derivative to the n-valent organic radical of the formula (III).

Here, in formula (III), n is very preferably an integer from the range from 3 to 10, in particular from 3 to 6. Here, q is very preferably an integer from the range from 2 to 10, particularly preferably from the range from 2 to 4, particularly preferably 2 or 3, in particular 2. Here, $R^{76}$ is very preferably H, aryl, $C_1$-$C_{30}$-alkyl, preferably $C_2$-$C_{20}$-alkyl, particularly preferably $C_{10}$-$C_{20}$-alkyl, in particular $C_{18}$-alkyl or $C_{20}$-alkyl.

In a further preferred embodiment of the invention, those benzotriazole derivatives are used in which the group A corresponds to an n-valent organic radical of the general formula (IIIa)

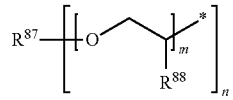

(IIIa)

where n is an integer from the range from 3 to 20, m independently of the others is an integer from the range 0 to 10, $R^{87}$ is a linear or branched $C_1$-$C_{20}$-alkane in which n hydrogens are replaced by a bond, $R^{88}$ is H, linear or branched $C_1$-$C_{20}$-alkyl, where * designates the bonding of the benzotriazole derivatives to the n-valent organic radical of the formula (IIIa). Here, in formula (IIIa), n is very preferably an integer from the range from 3 to 10, in particular from 3 to 6. m is very preferably an integer from 0 to 5, in particular from 0 to 3. $R^{87}$ is very preferably a $C_1$-$C_{10}$-alkane, in particular a $C_1$-$C_5$-alkane in which n hydrogens are replaced by a bond. Here, $R^{88}$ is very preferably H or methyl.

In a further preferred embodiment of the invention, those benzotriazole derivatives are used in which the group A corresponds to an n-valent organic radical of the general formula (IIIb)

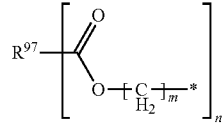

(IIIb)

where
n is an integer from the range from 3 to 20,
m independently of the others is an integer from the range 0 to 10,
$R^{97}$ is a linear or branched $C_1$-$C_{20}$-alkane in which n hydrogens are replaced by a bond where * designates the bonding of the benzotriazole derivatives to the n-valent organic radical of the formula (IIIb). Here, in formula (IIIb), n is very preferably an integer from the range from 3 to 10, in particular from 3 to 6. m is very preferably an integer from 0 to 5, in particular from 0 to 3. $R^{97}$ is very preferably a $C_1$-$C_{10}$-alkane, in particular a $C_1$-$C_5$-alkane in which n hydrogens are replaced by a bond.

In a further preferred embodiment of the invention, those benzotriazole derivatives are used in which the group A corresponds to a trivalent organic radical of the general formula (IIIc)

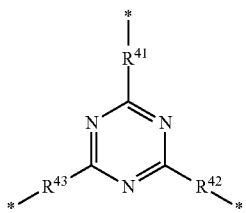

(IIIc)

where
$R^{41}$, $R^{42}$, $R^{43}$ independently of one another are $C_1$-$C_{20}$-alkylene,
where * designates the bonding of the benzotriazole derivatives to the trivalent organic radical of the formula (IIIc). Very preferably, $R^{41}$, $R^{42}$, $R^{43}$, independently of one another, are $C_1$-$C_5$-alkylene, in particular $C_2$-$C_3$-alkylene. Preferably, $R^{41}$, $R^{42}$, $R^{43}$ are all the same.

In a further preferred embodiment of the invention, those benzotriazole derivatives are used in which the group A corresponds to a trivalent organic radical of the general formula (IIId)

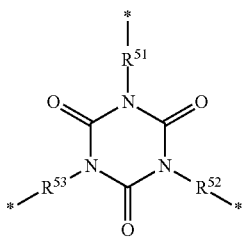

(IIId)

where
$R^{51}$, $R^{52}$, $R^{53}$ independently of one another are $C_1$-$C_{20}$-alkylene,
where * designates the bonding of the benzotriazole derivatives to the trivalent organic radical of the formula (IIId). Very preferably, $R^{51}$, $R^{52}$, $R^{53}$, independently of one another, are $C_1$-$C_5$-alkylene, in particular $C_2$-$C_3$-alkylene.

In a further preferred embodiment of the invention, those benzotriazole derivatives are used in which the group A corresponds to a tetravalent organic radical of the general formula (IIIe)

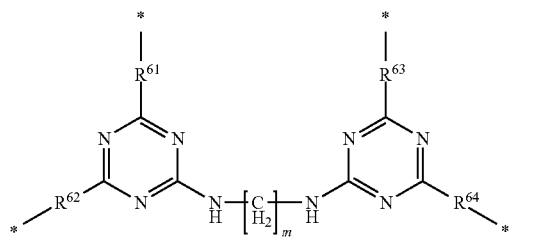

(IIIe)

where
$R^{61}$, $R^{62}$, $R^{63}$, $R^{64}$ independently of one another are $C_1$-$C_{20}$-alkylene,
where * designates the bonding of the benzotriazole derivatives to the tetravalent organic radical of the formula (IIIe). Very preferably, $R^{61}$, $R^{62}$, $R^{63}$, $R^{64}$, independently of one another, are $C_1$-$C_5$-alkylene, in particular $C_2$-$C_3$-alkylene. Preferably, $R^{61}$, $R^{62}$, $R^{63}$, $R^{84}$ are all the same.

In a further embodiment of the invention, the linkage of the n-valent organic radical A to the aforementioned benzotriazole derivatives of the general formulae (Ia), (Ib) or (Ic) takes place via the reaction of an at least n-hydric alcohol A' with a compound of the general formulae (IV), (IVa) or (V)

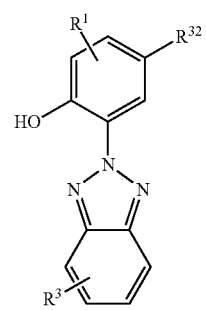

(IV)

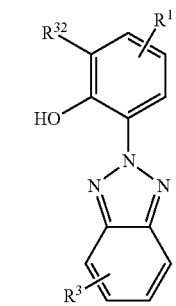

(IVa)

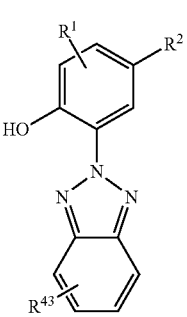

(V)

where
R$^{32}$, R$^{43}$ are a single bond or a group of the general formula (VI)

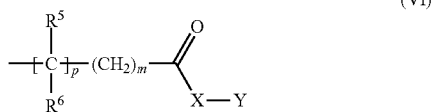

m is an integer from the range from 0 to 4,
p is 0 or 1,
X is O, NR$^7$,
R$^7$ is H, C$_1$-C$_{20}$-alkyl, C$_1$-C$_{20}$-alkoxy,
Y is H, C$_1$-C$_{20}$-alkyl, C$_1$-C$_{20}$-alkoxy,
with the proviso that at least three benzotriazole derivatives of the general formulae (IV), (IVa) or (V) are reacted with in each case one n-hydric alcohol A'. The other substituents here have the meanings given above for the formulae (Ia), (Ib) and (Ic). Very preferably, m in formula (VI) is an integer from the range from 0 to 4, particularly preferably from 1 to 3, very particularly preferably 1 or 2, in particular 2. Here, p is very preferably 0 or 1, particularly preferably 0 and likewise particularly preferably 1.

The n-hydric alcohol A' used is preferably a triol, tetrol, pentol, hexol or polyol. Very preferred triols are trimethylolpropane, glycerol. A preferred tetrol is pentaerythritol, a preferred pentol is sorbitol and a preferred hexol is mannitol.

In one preferred embodiment of the use according to the invention, the benzotriazole derivatives listed above are used as UV absorbers in plastics or waxes, where the plastics comprise, for example, polyolefins, such as polyethylene (PE) or polypropylene (PP), polycarbonates, polyesters, such as polyethylene terephthalate (PET), polyvinyl chloride (PVC), polystyrene (PS), polystyrene copolymers, such as high-impact modified PS (HIPS), styrene-acrylonitrile copolymer (SAN), acrylonitrile-styrene-acrylate copolymer (ASA), or acrylonitrile-butadiene-styrene copolymer (ABS), or polyolefin waxes. Plastics may also comprise or be copolymers or mixtures (blends) of said polymers. Preferred plastics are polyolefins and polycarbonates.

Incorporation of the benzotriazole derivatives into inanimate organic materials, in particular into plastics, generally takes place by mixing the constituents. For example, the mixing takes place by methods known to the person skilled in the art, as are generally used in the additization of plastics. The benzotriazole derivatives, in solid, liquid or dissolved form, are preferably used for the finishing of plastics. For this purpose, the benzotriazole derivatives can be incorporated into the plastics either as a solid or liquid formulation, or else as powders by customary methods. Mention is to be made here, for example, of the mixing of the particles with the organic polymers before or during an extrusion step. Further examples of the finishing or stabilization of plastics with additives can be found in the Plastics Additives Handbook, 5th edition, Hanser Verlag, ISBN 1-56990-295-X. The additivated plastics can be present, for example, as granules, pellets, powders, films or fibers.

In a further preferred embodiment of the use according to the invention, the benzotriazole derivatives listed above are used as UV absorbers in plastic moldings. Plastic moldings are preferably agricultural films, injection moldings, which may be colored, PC sheets, PET fibers, PET packagings, flame-retarded PP fibers, packaging films, in particular made of PE, food packagings, and candles. Particular preference is given to packaging films, in particular made of PE.

Production of plastic moldings takes place by methods known to the person skilled in the art. In particular, the plastic moldings can be produced by extrusion or coextrusion, compounding, processing of granules or pellets, injection molding, blow molding or kneading. Preferably, the processing takes place by extrusion or coextrusion to give films (cf. Saechtling Kunststoff Taschenbuch [Plastics Handbook], 28th edition, Karl Oberbach, 2001).

The inanimate organic materials, in particular the plastics or plastic moldings, comprise from 0.01 to 10% by weight of the benzotriazoles listed above, based on the total amount of inanimate organic material or plastic. In one embodiment, preferably from 0.05 to 1% by weight of benzotriazole derivatives are added to it. In another embodiment, preferably from 5 to 8% by weight of benzotriazole derivatives are added.

In a special embodiment, the inanimate organic materials, in particular the plastics or plastic moldings, comprise a thermoplastic polymer component or consist of a thermoplastic polymer component. Thermoplasts are characterized by their good processability and can be processed in the softened state to give moldings e.g. by compression, extrusion, injection molding or other shaping methods.

The inanimate organic materials, in particular the plastics or plastic moldings, can additionally comprise at least one further additive that is preferably selected from colorants, antioxidants, stabilizers, e.g. hindered amine light stabilizers (HALS), other UV absorbers, nickel quenchers, metal deactivators, reinforcers and fillers, antifogging agents, biocides, acid scavengers, antistats, IR absorbers for long-wave IR radiation, antiblocking agents such as SiO2, light-scattering agents such as MgO or TiO2, inorganic or organic reflectors (for example aluminum flakes).

The total amount of optional further additives in the composition is up to 15% by weight, based on the total amount of inanimate organic material or plastic. Preferably, the amount of these additives is 0.5 to 15% by weight, very preferably 0.5 to 10% by weight and in particular 0.5 to 7.5% by weight.

In this connection, optional further stabilizers that are to be mentioned are, for example, phosphites, phosphonites, phosphines, hindered amines (HALS compounds), hydroxylamines, phenols, phenols modified with acryloyl, peroxide decomposers, benzofuranone derivatives or mixtures of these. Stabilizers are often commercially available, for example under the following trade names IRGAPHOS® 168, DOVERPHOS® S-9228, ULTRANOX® 641 from Ciba and Dover. Furthermore, in addition to the stabilizers, it is also possible to use costabilizers in order to increase the thermal stability.

Preferred optional further stabilizers as further additives are phosphites or HALS compounds. HALS compounds from Ciba, which are available under the trade names Chimassorb®, in particular Chimasorb® 119 FL, 2020, 940, or Tinuvin®, in particular Tinuvin® 111, 123, 492, 494, 622, 765, 770, 783, 791, C 353, are very preferred. HALS compounds from BASF SE which are available under the trade name Uvinul®, in particular Uvinul® 4050 H (CAS No. 124172-53-8), Uvinul® 4077 H (CAS No. 52829-07-9) or Uvinul® 5050 H (CAS No. 152261-33-1) are likewise very preferred.

In general, the optional stabilizers are used as further additives in an amount of from 0.001 to 3% by weight, based on the total amount of inanimate organic material or plastic, preferably from 0.002 to 2% by weight, very preferably from 0.003 to 1% by weight and in particular from 0.005 to 0.5% by weight.

Suitable optional further UV absorbers are, for example, the commercially available compounds of Tinuvin®, in particular Tinuvin® 234, 326, 327, 328 or Uvinul® product families from Ciba or BASF SE, respectively.

The Uvinul® photoprotective agents comprise compounds of the following classes:

benzophenones, benzotriazoles, cyanoacrylates, cinnamic acid esters, para-aminobenzoates, naphthalimides. Moreover, further known chromophores are used, e.g. hydroxyphenyltriazines or oxalanilides.

Further examples of optional further UV absorbers are:

substituted acrylates, such as, for example, ethyl or isooctyl α-cyano-β,β-diphenylacrylate (predominatly 2-ethylhexyl α-cyano-β,β-diphenylacrylate), methyl α-methoxycarbonyl-β-phenylacrylate, methyl α-methoxycarbonyl-β-(p-methoxyphenyl) acrylate, methyl or butyl α-cyano-β-methyl-β-(p-methoxyphenyl)acrylate, N-(β-methoxycarbonyl-β-cyanovinyl)-2-methylindoline, octyl p-methoxycinnamate, isopentyl 4-methoxycinnamate, urocaninic acid or salts or esters thereof;

derivatives of p-aminobenzoic acid, in particular esters thereof, for example ethyl 4-aminobenzoate, or ethoxylated ethyl 4-aminobenzoates, salicylates, substituted cinnamic acid esters (cinnamates) such as octyl p-methoxycinnamate or 4-isopentyl-4-methoxycinnamate, 2-phenylbenzimidazole-5-sulfonic acid or its salts;

2-hydroxybenzophenone deriviates, such as, for example, 4-hydroxy-, 4-methoxy-, 4-octyloxy-, 4-decyloxy-, 4-dodecyloxy-, 4-benzyloxy-, 4,2',4'-trihydroxy-, 2'-hydroxy-4,4'-dimethoxy-2-hydroxybenzophenone and 4-methoxy-2-hydroxybenzopheone sulfonic acid sodium salt;

esters of 4,4-diphenylbutadiene-1,1-dicarboxylic acid, such as, for example, the bis(2-ethylhexyl) esters;

2-phenylbenzimidazole-4-sulfonic acid and 2-phenylbenzimidazole-5-sulfonic acid or salts thereof;

derivatives of benzoxazoles;

derivatives of benzotriazoles or 2-(2'-hydroxyphenyl)benzotriazoles, such as, for example, 2-(2H-benzotriazol-2-yl)-4-methyl-6-(2-methyl-3-((1,1,3,3-tetramethyl-1-(trimethylsilyloxy)disiloxanyl)propyl)phenol, 2-(2'-hydroxy-5'-methylphenyl)-benzotriazole, 2-(3',5'-ditert-butyl-2'-hydroxyphenyl)benzotriazole, 2-(5'-tert-butyl-2'-hydroxyphenyl)benzotriazole, 2-[2'-hydroxy-5'-(1,1,3,3-tetramethylbutyl)phenyl]-benzotriazole, 2-(3',5'-ditert-butyl-2'-hydroxyphenyl)-5-chlorobenzotriazole, 2-(3'-tert-butyl-2'-hydroxy-5'-methylphenyl)-5-chllorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-[3',5'-bis(α,α-dimethylbenzyl)-2'-hydroxyphenyl]benzotriazole, 2-[3'-tert-butyl-2'-hydroxy-5'-(2-octyloxycarbonylethyl)-phenyl]-5-chlorobenzotriazole, 2-[3'-tert-butyl-5'-(2-(2-ethylhexyloxy)carbonylethyl)-2'-hydroxyphenyl]-5-chlorobenzotriazole, 2-[3'-tert-butyl-2'-hydroxy-5'-(2-methoxy-carbonyletyl)phenyl]-5-chlorobenzotriazole, 2-[3'-tert-butyl-2'-hydroxy-5'-(2-methoxy-carbonylethyl)phenyl]benzotriazole, 2-[3'-tert-butyl-2'-hydroxy-5'-(2'-octyloxycarbonyl-ethyl)phenyl]benzotriazole, 2-[3'-tert-butyl-5'-(2-(2-ethylhexyloxy)carbonylethyl)-2'-hydroxyphenyl]benzotriazole, 2-(3'-dodecyl-2'-hydroxy-5'-methylphenyl)-benzotriazole, 2-[3'-tert-butyl-2'-hydroxy-5'-(2-isooctyloxycarbonylethyl)phenyl]-benzotriazole, 2,2'-methylenebix[4-(1,1,3,3-tetramethylbutyl)-6-benzotriazol-2-ylphenol], the completely esterified product of 2-[3'-tert-butyl-5'-(2-methoxycarbonyl-etyl)-2'-hydroxyphenyl]-2H-benzotriazole with polyethylene glycol 300, [R—CH2CH2-COO(CH2)3-]2 where R is 3'-tert-butyl-4-hydroxy-5'-2H-benzotriazol-2-ylphenyl, 2-[2'-hydroxy-3'-(α,α-dimetylbenzyl)-5'-(1,1,3,3-tetramethylbutyl)phenyl]benzotriazole, 2-[2'-hydroxy-3'-(1,1,3,3-tetrametylbutyl)-5'-(α,α-dimethylbenzyl)phenyl]benzotriazole;

benzylidenecamphor or its derivatives, as are specified, for example, in DE-A 38 36 630, e.g. 3-benzylidenecamphor, 3-(4'-methylbenzylidene)-dl-camphor;

α-(2-oxoborn-3-ylidene)toluene-4-sulfonic acid or its salts, N,N,N-trimethyl-4-(2-oxoborn-3-ylidenemethyl) anilinium monosulfate;

dibenzoylmethanes, such as, for example, 4-tert-butyl-4'-methoxydibenzoylmethane;

2,4,6-triaryltriazine compounds such as 2,4,6-tris{N-[4-(2-ethylhex-1-yl)oxycarbonylphenyl]amino}-1,3,5-triazine, bis(2'-ethylhexyl)-4,4'-((6-(((tert-butyl)aminocarbonyl)phenylamino)-1,3,5-triazine-2,4-diyl)imino)bisbenzoate;

2-(2-hydroxyphenyl)-1,3,5-triazines, such as, for example, 2,4,6-tris(2-hydroxy-4-octyloxyphenyl)1,3,5-triazine, 2-(2-hydroxy-4-octyloxyphenyl)-4,6-bis(2,4-dimethyl-phenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4(2-hydroxy-3-dodecyloxypropoxy)phenyl]-4,6-bis(2,4-dimethylphenyl)-1,3,5-triazine, 2-(2-hydroxy-4-hexyloxyphenyl)-4,6-diphenyl-1,3,5-triazine, 2-(2-hydroxy-4-methoxyphenyl)4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ehylhexyl-1-oxy)-2-hydroxypropyloxy]phenyl}-4,6-bis(2,4-dimethylphenyl)-1,3,5-triazine.

Suitable optional further UV absorbers can be found in the publication Cosmetic Legislation, Vol. 1, Cosmetic Products, European Commission 1999, pp. 64-66, to which reference is hereby made.

Moreover, suitable optional further UV absorbers are described in lines 14 to 30 ([0030]) on page 6 of EP 1 191 041 A2. Reference is made to the contents of this in their entirety.

The optional further UV absorbers, if present, are generally used in an amount of from 0.01% by weight to 10% by weight, based on the total amount of inanimate organic material or plastic. Preference is given to using from 0.05 to 8% by weight of UV absorber, very preferably from 0.1 to 7% by weight, in particular from 0.1 to 5% by weight.

These optional additives are added during the production of the inanimate organic materials, in particular the plastics or plastic moldings, or in the course of optional additional steps in the process.

In a further preferred embodiment of the use according to the invention, the benzotriazole derivatives listed above are used as UV absorbers in textiles, preferably in clothing for bathing, outer clothing or outdoor clothing.

In a further preferred embodiment of the use according to the invention, the benzotriazole derivatives listed above are used as UV absorbers in cosmetic preparations.

In a further preferred embodiment of the use according to the invention, the benzotriazole derivatives listed above are used as photoprotective agents and stabilizers for plastics.

The invention further provides a method of stabilizing plastics against the effect of light, optionally in conjunction with the additional effect of oxygen on the plastic, which comprises using for this the benzotriazole derivatives listed above. Here, from 0.01% to 10% by weight, based on the amount of the plastic, of the benzotriazole derivatives listed above are added to the plastics. In one embodiment, preferably from 0.05% to 1% by weight of benzotriazole derivatives are added to the plastic. In another embodiment, preferably from 5 to 8% by weight of benzotriazole derivatives are added to the plastic.

The invention further provides inanimate organic materials, in particular plastics, stabilized against the effect of light, oxygen and heat, comprising form 0.01 to 10% by weight, based on the amount of the inanimate organic material, of the benzotriazole derivatives listed above. In one embodiment, from 0.05 to 1% by weight of benzotriazole derivatives are preferably present in the plastic. In another embodiment, preferably from 5 to 8% by weight of benzotriazole derivatives are present in the plastic.

The invention further provides benzotriazole derivatives of the general formulae (Ia), (Ib) and (Ic) in which the group A corresponds to an n-valent organic radical of the general formula (III). The meaning of the other symbols and indices corresponds to the meaning in the formulae (Ia), (Ib), (Ic) and (III). Here, n is very preferably an integer from the range from 3 to 10, in particular from 3 to 6. Here, q is very preferably an integer from the range from 2 to 10, particularly preferably from the range from 2 to 4, especially preferably 2 or 3, in particular 2. Here, $R^{76}$ is very preferably H, aryl, $C_1$-$C_{30}$-alkyl, preferably $C_2$-$C_{20}$-alkyl, particularly preferably $C_{10}$-$C_{20}$-alkyl, in particular $C_{18}$-alkyl or $C_{20}$-alkyl.

The invention further provides benzotriazole derivatives of the general formulae (Ia), (Ib) and (Ic) in which the group A corresponds to an n-valent organic radical of the general formula (IIIa). The meaning of the other symbols and indices corresponds to the meaning in the formulae (Ia), (Ib), (Ic) and (IIIa). Here, in formula (IIIa), n is very preferably an integer from the range from 5 to 10, in particular from 5 to 6. m is very preferably an integer from 0 to 5, in particular 0. $R^{87}$ is very preferably a $C_1$-$C_{10}$-alkane, in particular a $C_1$-$C_5$-alkane in which n hydrogens are replaced by a bond.

Particular preference is given here to benzotriazole derivatives of the general formulae (Ia), (Ib) and (Ic) in which the group A corresponds to an n-valent organic radical of the general formula (IIIa) and n=5, 6, $R^{87}$ is a $C_1$-$C_{10}$-alkane, in particular a $C_1$-$C_5$-alkane in which n hydrogens are replaced by a bond, and $R^2$, $R^{12}$, $R^{23}$ are O.

The invention further provides benzotriazole derivatives of the general formulae (Ia), (Ib) and (Ic) in which the group A corresponds to an n-valent organic radical of the general formula (IIIb). The meaning of the remaining symbols and indices corresponds to the meaning in the formulae (Ia), (Ib), (Ic) and (IIIb). Here, in formula (IIIb), n is very preferably an integer from the range from 5 to 10, in particular from 5 to 6. m is very preferably an integer from 0 to 5, in particular 2 or 3. $R^{97}$ is very preferably a $C_1$-$C_{10}$-alkane, in particular a $C_1$-$C_5$-alkane in which n hydrogens are replaced by a bond.

The molecular weight (number-average Mn) of the benzotriazole derivatives of the general formulae (I), (Ia), (Ib) or (Ic) is preferably from 1100 g/mol to 5000 g/mol, particularly preferably from 1500 to 5000 g/mol, in particular from 2000 to 5000 g/mol.

The invention further provides benzotriazole derivatives prepared by the preferred process.

The present invention provides UV absorbers and stabilizers which only escape from inanimate organic materials, in particular plastics, only to a very slight extent. The suppression of the migration offers advantages here, such as, for example, a prolonged stabilizing effect or an avoidance of effects of the substances hazardous to health, for example upon contact of the substances with foods.

The invention is illustrated in more detail by the examples without the examples limiting the subject matter of the invention.

EXAMPLES

Various benzotriazole derivatives were synthesized by the following procedures.

Data relating to molecular mass, adsorption parameters and melting points can be found in Table 1.

Room temperature: 21° C.

Example 1

Oligoether Amines

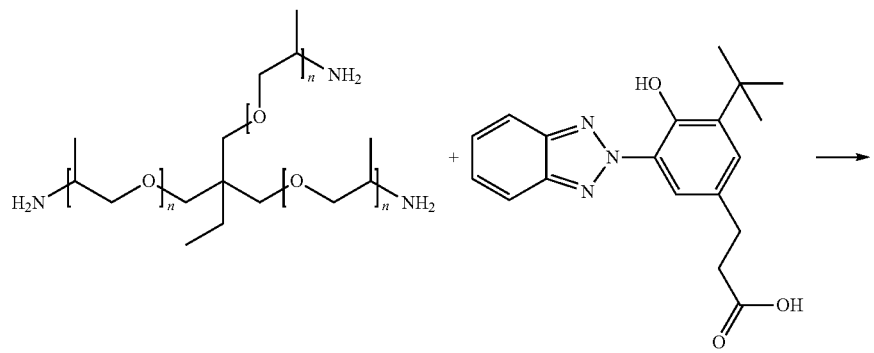

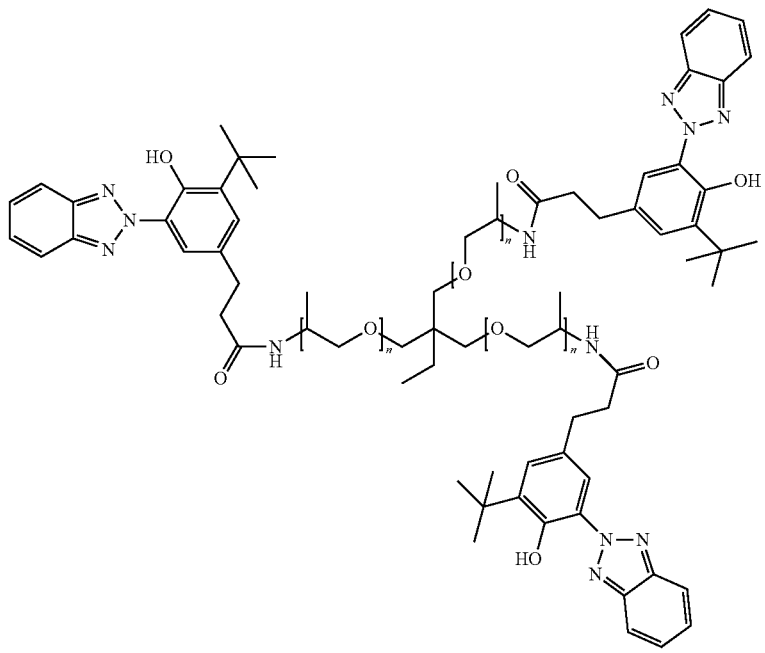

Under a nitrogen atmosphere, 13.6 g (0.04 mol) of 3-(3-benzotriazol-2-yl-5-tert-butyl-4-hydroxyphenyl)propionic acid and 6.3 g (0.0143 mol) of polyether amine (M=440 g/mol) were initially introduced at room temperature. The mixture was stirred at 200° C. for 5 h, during which the water of reaction which formed was removed azeotropically. Upon cooling to room temperature, the reaction mixture became solid, and 17.5 g of the crystalline product (84% yield) were obtained.

Example 2

Maleic Anhydride (MA) Derivatives

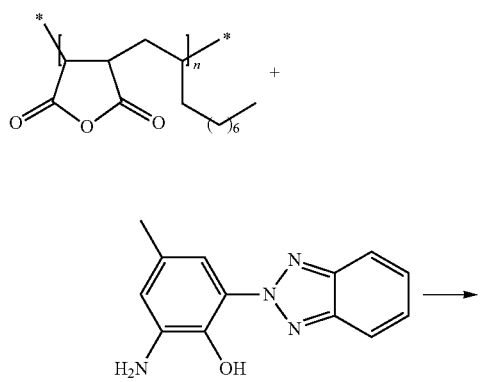

Under a nitrogen atmosphere, 8.65 g (0.02 mol) of MA α-olefin (n=1.8) (50.6% strength dissolved in Solvesso 150) and 4.81 g (0.02 mol) of 2-amino-6-benzotriazol-2-yl-4-methylphenol in 40 ml of Solvesso 150 (napththa cut: mixture of heavy aromatic hydrocarbons) were initially introduced at room temperature. The mixture was stirred under reflux at 175° C. for 20 h, during which the water of reaction which formed was removed azeotropically. Upon cooling to room temperature, the product precipitated out. The residue was filtered off with suction and washed with petroleum ether. The solvent was removed from the organic phase in vacuo. The residue obtained was dissolved in acetic ester and stirred with activated carbon for 1 h at RT. The activated carbon was filtered off and the solvent was removed in vacuo. This gave 4.37 g of crystalline product.

Example 3

Further MA Derivatives

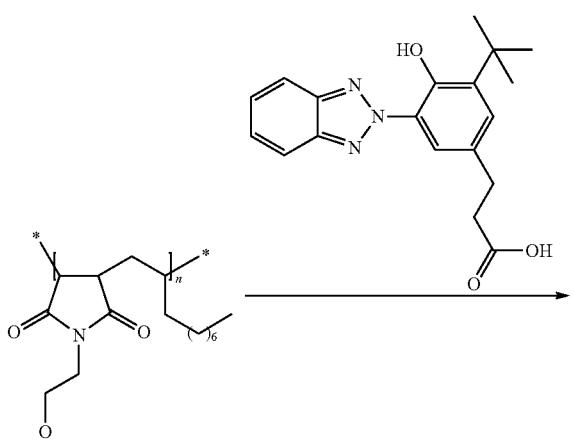

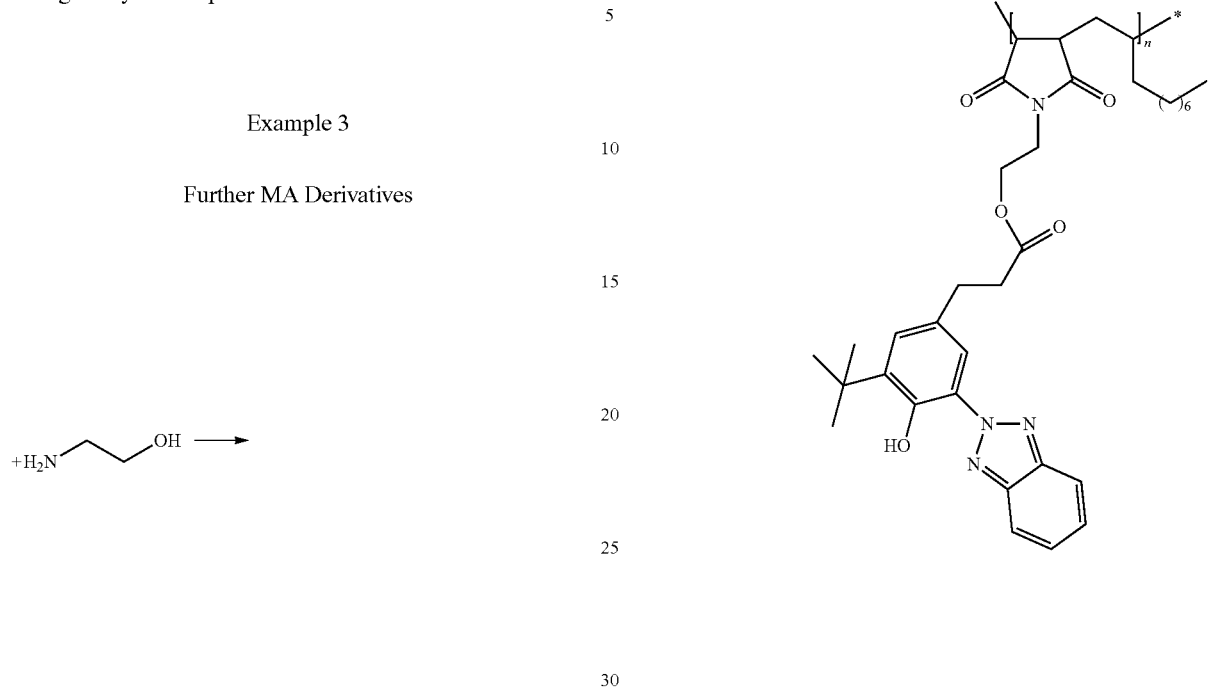

Under a nitrogen atmosphere, 8.65 g (0.02 mol) of MA α-olefin CP decene (n=1.8) and 2.4 g (0.04 mol) of ethanolamine were initially introduced at room temperature and then stirred under reflux at 163° C. for 2 h, during which the water of reaction which formed was removed azeotropically. The mixture was cooled to 120° C. 13.6 g (0.04 mol) of 3-(3-benzotriazol-2-yl-5-tert-butyl-4-hydroxyphenyl)propionic acid and 0.2 g of p-toluenesulfonic acid monohydrate were added. The reaction mixture was stirred for 6 h at 163° C. and then cooled to room temperature. 200 ml of dichloromethane and 10 g of silica gel were added. The mixture was stirred for 1 h at room temperature. The silica gel was separated off and the solvent was removed in vacuo. 11.7 g of crystalline product were obtained.

Example 4

Carboxylic Acid Derivatives

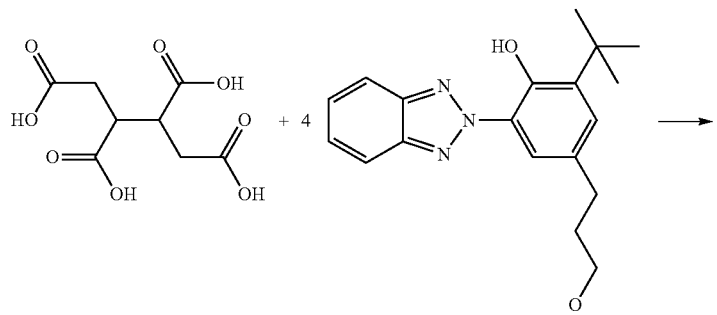

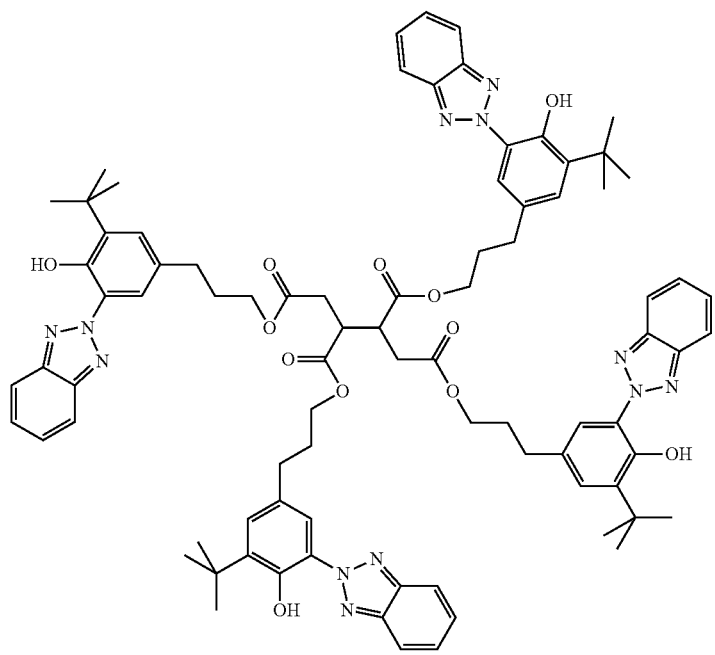

Under a nitrogen atmosphere, 2.3 g (0.01 mol) of 1,2,3,4-butanetetracarboxylic acid, 13.0 g (0.04 mol) of 2-(2'-hydroxy-5'-hydroxypropylphenyl)-2H-benzotriazole and 0.15 ml (0.002 mol) of methanesulfonic acid in 75 ml of Solvesso 100 (naphtha cut: mixture of light aromatic hydrocarbons) were initially introduced at room temperature and then stirred under reflux at 165° C. for 24 h, during which the water of reaction which formed was removed azeotropically. The mixture was cooled to room temperature and the solvent was removed in vacuo. 500 ml of petroleum ether were added to the residue. The mixture was stirred for 1 h at room temperature. The suspension was filtered off with suction via a frit. The residue was washed with a small amount of petroleum ether and dried in a vacuum cabinet at 60° C. This gave 13.8 g of colorless crystalline product (94% yield).

Example 5

Cyanuric Acid Derivatives

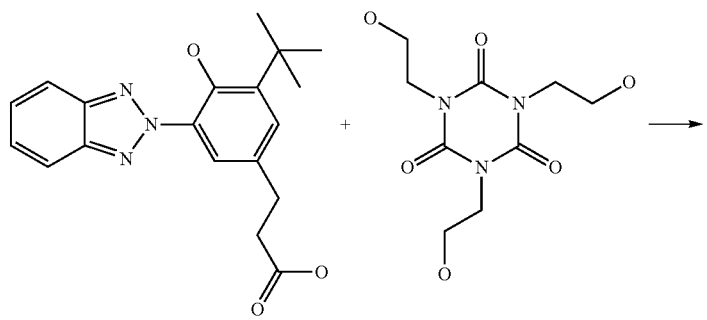

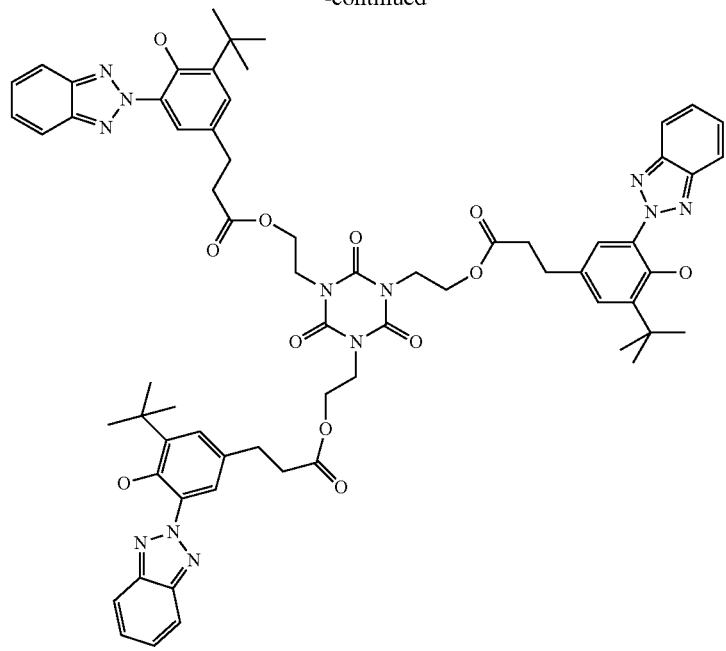

Under a nitrogen atmosphere, 6.5 g (0.0025 mol) of 1,3,5-tris(2-hydroxyethyl)cyanuric acid, 25.5 g (0.075 mol) of 3-(3-benzotriazole-2-yl-5-tert-butyl-4-hydroxyphenyl)propionic acid and 0.5 ml (0.009 mol) of methanesulfonic acid in 150 ml of xylene were initially introduced at room temperature and then stirred for 4 days at 140° C. (reflux), during which the water of reaction which formed was removed azeotropically. The mixture was cooled to room temperature and the solvent was removed in vacuo. The residue obtained was purified by means of column chromatography (100 toluene: 2.5 acetic ester). This gave 16.2 g of crystalline product (53% yield).

Example 6

Cyanuric Chloride Derivatives

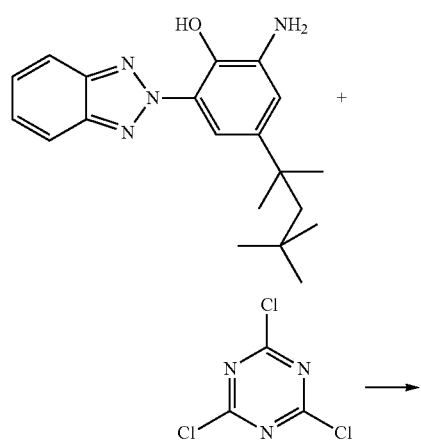

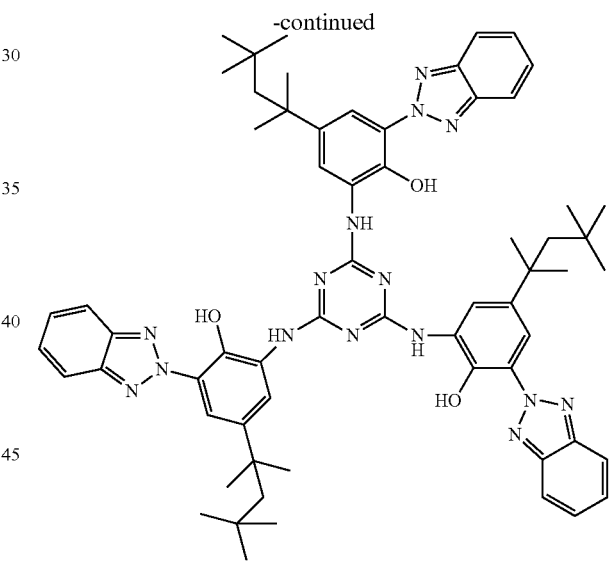

Under a nitrogen atmosphere, 1.8 g (0.01 mol) of cyanuric chloride, 10.15 g (0.03 mol) of 2-amino-6-benzotriazol-2-yl-4-tert-octylphenol and 2.5 g (0.03 mol) of sodium hydrogencarbonate in a solvent mixture of 15 ml of dimethylformamide (DMF) and 4.5 ml of 1,4-dioxane were initially introduced at room temperature. The mixture was stirred at reflux (102° C.) for 24 h and then cooled to room temperature. The suspension was filtered off with suction over a frit. The residue was washed with water and dried at 50° C. in a vacuum cabinet. 9.32 g of a crystalline product (85.5% yield) were obtained.

Example 7

Further Cyanuric Chloride Derivatives

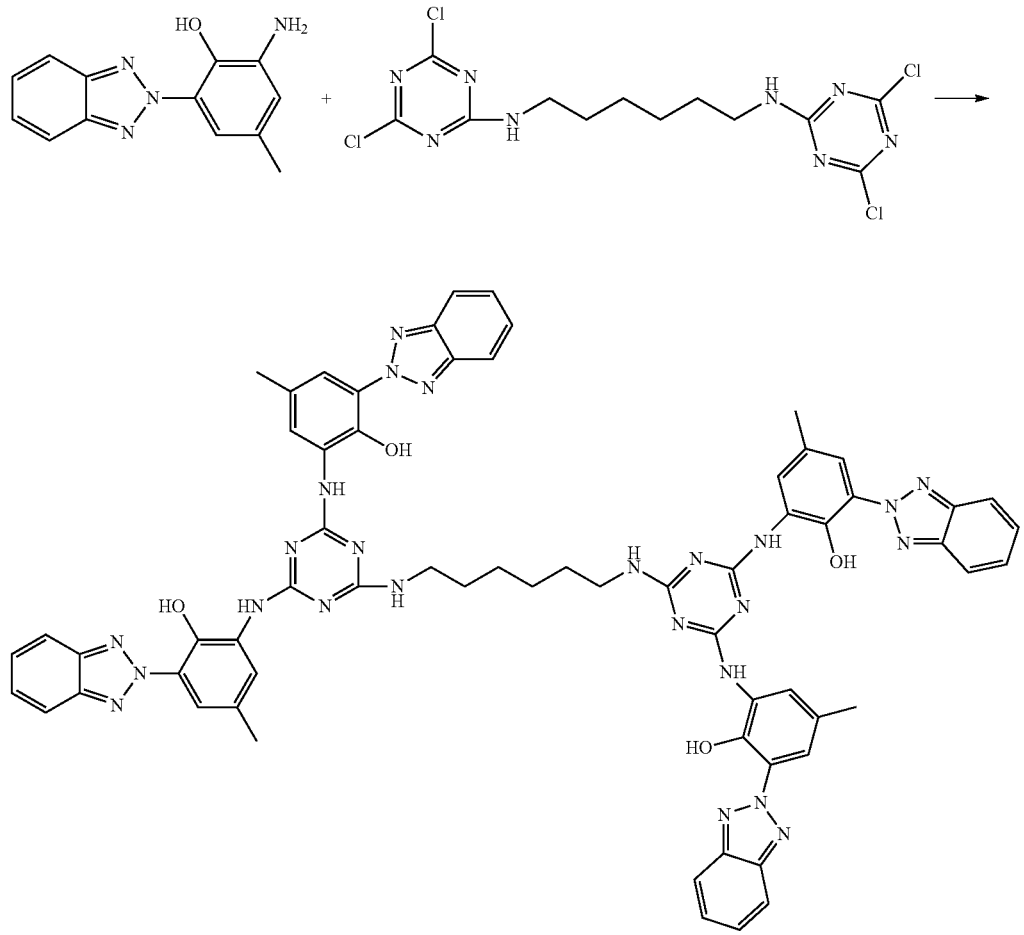 [SMILES: Cc1cc(N)c(O)c(-n2nc3ccccc3n2)c1 ; Clc1nc(Cl)nc(NCCCCCCNc2nc(Cl)nc(Cl)n2)n1 ; Cc1cc(Nc2nc(NCCCCCCNc3nc(Nc4cc(C)cc(-n5nc6ccccc6n5)c4O)nc(Nc4cc(C)cc(-n5nc6ccccc6n5)c4O)n3)nc(Nc3cc(C)cc(-n4nc5ccccc5n4)c3O)n2)c(O)c(-n2nc3ccccc3n2)c1]

Under a nitrogen atmosphere, 1.29 g (0.003 mol) of N,N'-bis(4,6-dichloro[1,3,5]triazin-2-yl)hexane-1,6-diamine, 3.36 g (0.014 mol) of 2-amino-6-benzotriazol-2-yl-4-methylphenol and 0.83 g (0.01 mol) of sodium hydrogen carbonate in 20 ml of N-methyl-2-pyrrolidone were initially introduced at room temperature. The mixture was stirred for 24 h at 160° C. and then cooled to RT. 20 ml of methanol were added to the reaction mixture. It was after-stirred for 1 h at room temperature. The suspension was filtered off with suction over a frit. The residue was washed firstly with methanol and finally with water. The residue was dried at 50° C. in a drying cabinet. 9.97 g of a crystalline product (90% yield) were obtained.

Example 8

Derivatives with Propoxylated Triol

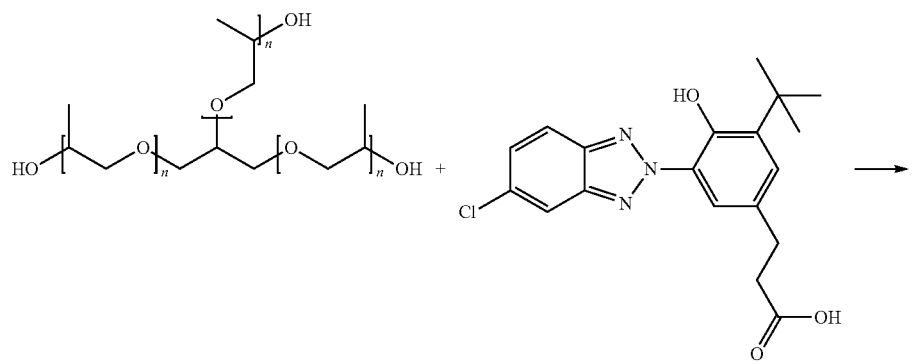

-continued

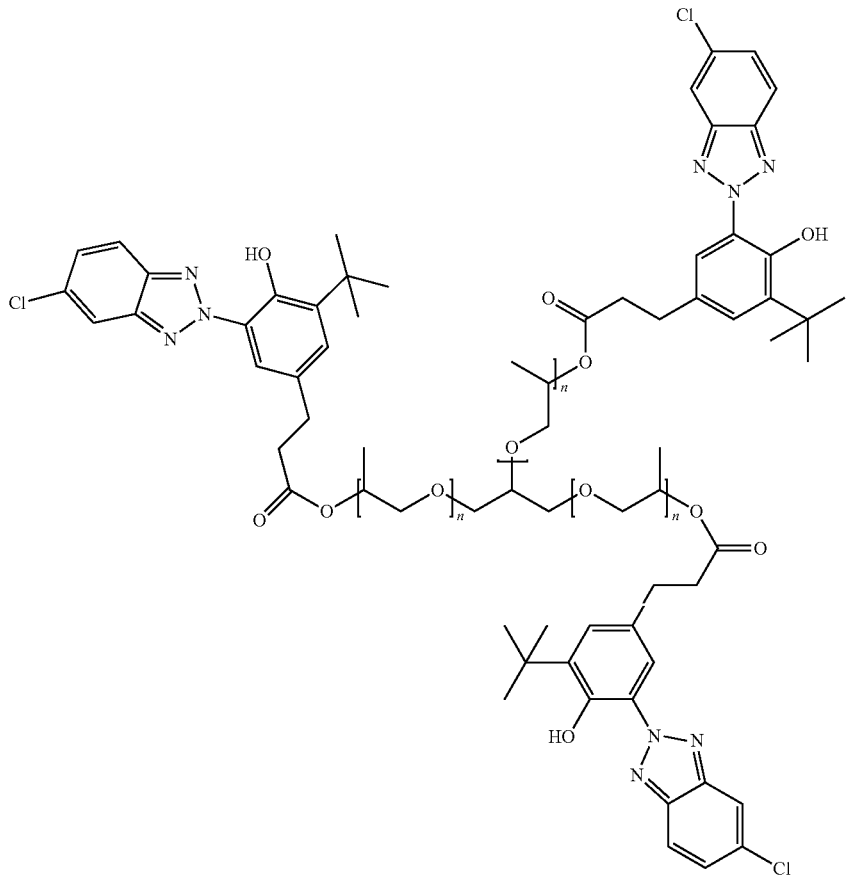

Under a nitrogen atmosphere, 14.9 g (0.04 mol) of 2-(5-chloro-2H-benzotriazol-2-yl)-6-tert-butyl-4-hydroxyphenylpropionic acid, 5.7 g (0.04 mol) of polyetherpolyol (Mw=420) and 0.35 ml (0.005 mol) of methanesulfonic acid in 200 ml of xylene were initially introduced at room temperature and then stirred at 140° C. (reflux) for 24 h, during which the water of reaction which formed was removed azeotropically. The mixture was cooled to room temperature and the solvent was removed in vacuo. The residue obtained was purified by means of column chromatography (100 toluene: 2.5 acetic ester). This gave 16.8 g of the product (90% yield).

Example 9

Diol Derivatives

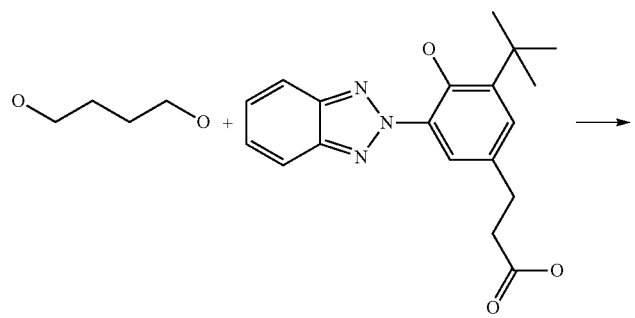

-continued

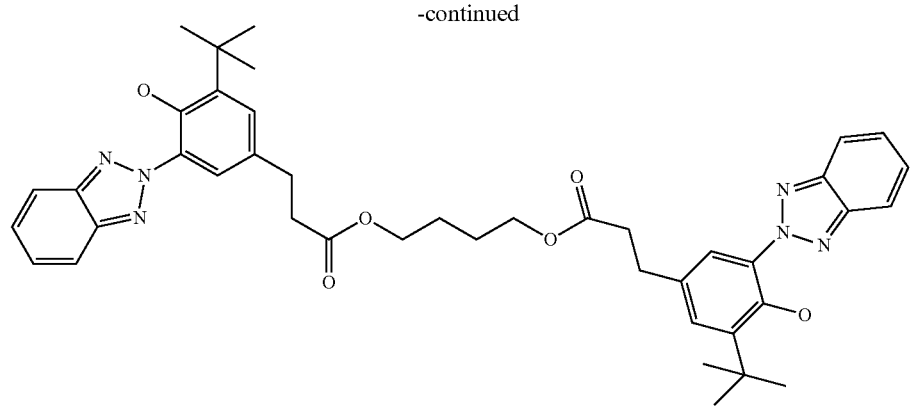

Under a nitrogen atmosphere, 23.8 g (0.07 mol) of 3-(3-benzotriazol-2-yl-5-tert-butyl-4-hydroxyphenyl) propionic acid, 3.15 g (0.035 mol) of 1,4-butanediol and 0.5 ml (0.008 mol) of methanesulfonic acid in 100 ml of xylene were initially introduced at room temperature and then stirred for 2 days at 140° C. (reflux), during which the water of reaction which formed was removed azeotropically. The mixture is cooled to room temperature and the solvent removed in vacuo. The residue obtained is purified by means of column chromatography (100 toluene: 2.5 acetic ester). 20.7 g of the crystalline product (80.5% yield) were obtained.

Example 10

Trishydroxymethylpropane Derivatives

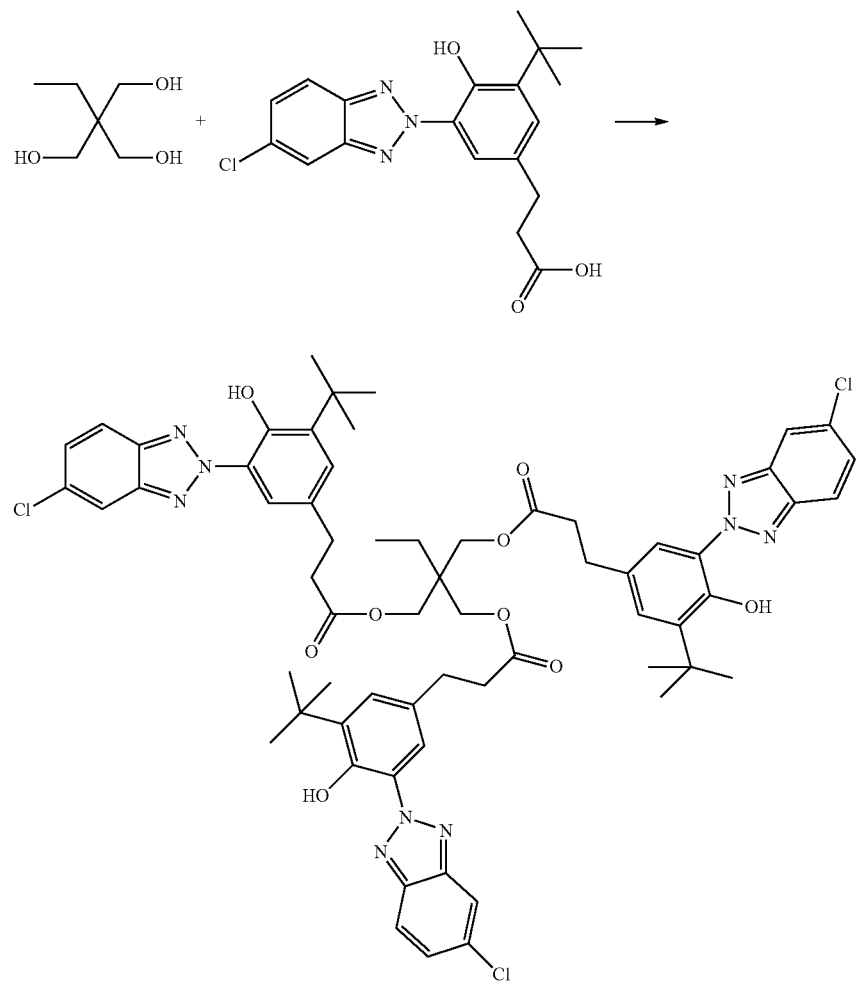

Under a nitrogen atmosphere, 16.8 g (0.045 mol) of 2-(5-chloro-2H-benzotriazol-2-yl)-6-tert-butyl-4-hydroxyphenylpropionic acid, 2.05 g (0.015 mol) of 1,1,1-tris(hydroxymethyl)propane and 0.58 ml (0.008 mol) of methanesulfonic acid in 150 ml of xylene were initially introduced at room temperature and stirred at 140° C. (reflux) for 4 days, during which the water of reaction which formed was removed azeotropically. The mixture was cooled to room temperature and the solvent was removed in vacuo. The residue obtained was purified by means of column chromatography (100 toluene: 2.5 acetic ester). This gave 11.2 g of the crystalline product (62% yield).

Example 11

Pentaerythritol Derivatives

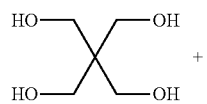

+

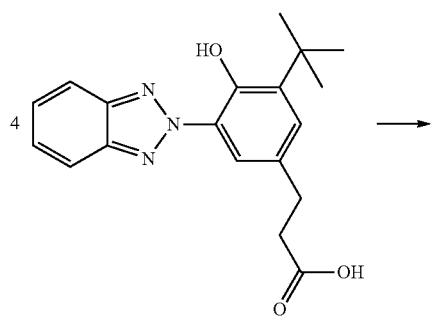

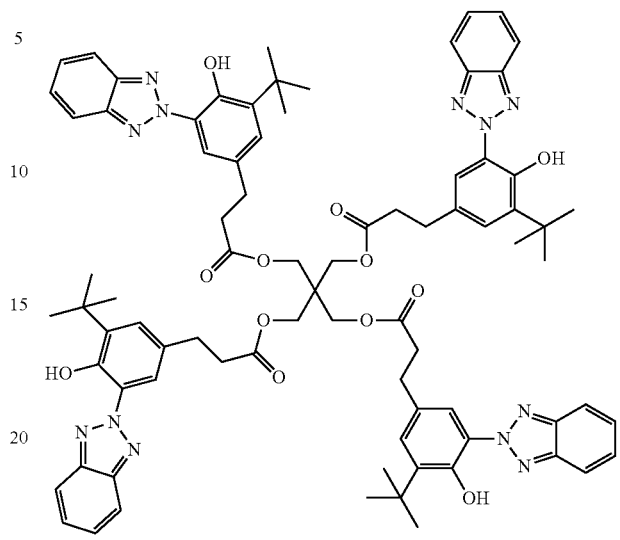

Under a nitrogen atmosphere, 17.0 g (0.05 mol) of 3-(3-benzotriazol-2-yl-5-tert-butyl-4-hydroxyphenyl) propionic acid, 1.7 g (0.0125 mol) of pentaerythritol and 0.50 ml (0.008 mol) of methanesulfonic acid in 100 ml of xylene were initially introduced at room temperature and then stirred at 140° C. (reflux) for 3 days, during which the water of reaction which formed was removed azeotropically. The mixture was cooled to room temperature and the solvent was removed in vacuo. The residue obtained was purified by means of column chromatography (100 toluene: 2.5 acetic ester). This gave 10.7 g of the crystalline product (60% yield).

Example 12

Further Pentaerythritol Derivatives

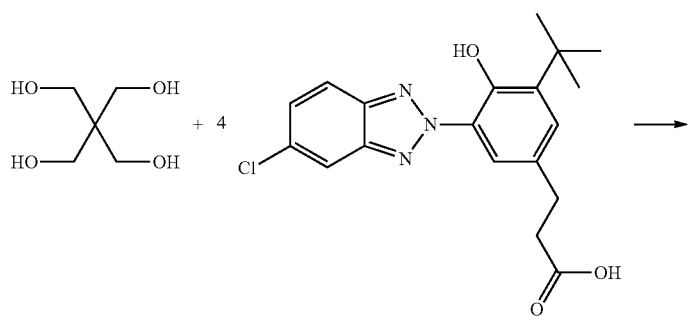

-continued

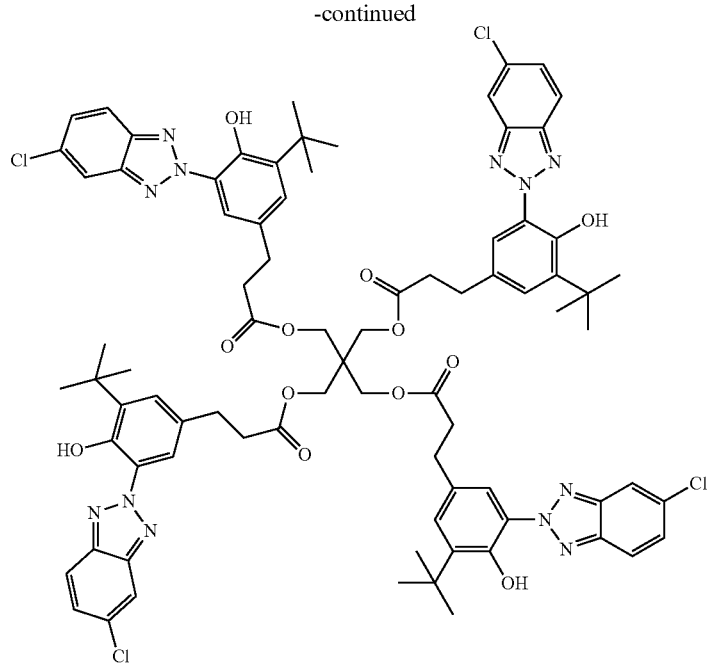

Under a nitrogen atmosphere, 18.7 g (0.05 mol) of 2-(5-chloro-2H-benzotriazol-2-yl)-6-tert-butyl-4-hydroxyphenylpropionic acid, 1.7 g (0.0125 mol) of pentaerythritol and 0.50 ml (0.008 mol) of methanesulfonic acid in 100 ml of xylene were initially introduced at room temperature and then stirred at 140° C. (reflux) for 3 days, during which the water of reaction which formed was removed azeotropically. The mixture was cooled to room temperature and the solvent was removed in vacuo. The residue obtained was purified by means of column chromatography (100 toluene: 2.5 acetic ester). This gave 10.1 g of the crystalline product (51% yield).

Table 1 below summarizes the physicochemical data for the compounds from the aforementioned examples and for the comparison substances. The UV spectra were measured in methylene chloride (apart from example 7: in NMP) in a concentration of 0.5 g/liter. The onset temperature (degradation temperature: T-onset) was measured by means of thermogravimetry under air, between 30° C. and 600° C. (heating rate=10° C. per minute). The T-onset value is a measure of the thermal stability of the substance and should achieve at least the temperature at which processing of the polymer takes place.

The substances from the examples exhibited overall an absorption in the UV comparable with the comparison substances. At a considerably higher molecular weight, these substances exhibit a comparable or higher extinction coefficient and a comparable or higher T-onset value relative to the comparison substances.

TABLE 1

| Example number | Peak position (nm) | Extinction coefficient [l/cm * g] | T-onset (° C.) | Molar mass (g/mol) |
|---|---|---|---|---|
| 1 | 342 | 30.6455 | 386.3 | ca. 1420 |
|   | 302 | 31.1545 |   |   |
| 2 | 336 | 24.2488 | 386.7 | >1100 |
|   | 298 | 23.9558 |   |   |
| 3 | 342 | 21.4761 | 379.9 | >1100 |
|   | 302 | 21.4652 |   |   |

TABLE 1-continued

| Example number | Peak position (nm) | Extinction coefficient [l/cm * g] | T-onset (° C.) | Molar mass (g/mol) |
|---|---|---|---|---|
| 4 | 342 | 40.1960 | 356.2 | 1463.76 |
|   | 302 | 40.9720 |   |   |
| 5 | 342 | 35.5310 | 379.2 | 1225.38 |
|   | 302 | 35.2793 |   |   |
| 6 | 324 | 66.5000 | 378.2 | 1090.4 |
|   | 276 | 70.6900 |   |   |
| 7 | 314 | 54.8833 | 419.2 | 1227.33 |
| 8 | 350 | 31.2560 | 328.5 | ca. 1400 |
|   | 310 | 27.4400 |   |   |
| 9 | 342 | 41.4160 | 355.5 | 732.89 |
|   | 302 | 40.9080 |   |   |
| 10 | 350 | 41.1840 | 376.5 | 1201.66 |
|   | 310 | 35.7960 |   |   |
| 11 | 342 | 42.2250 | 392.3 | 1421.68 |
|   | 302 | 41.9333 |   |   |
| 12 | 348 | 41.5960 | 377.1 | 1559.46 |
|   | 310 | 36.1320 |   |   |
| Comparison 1 | 342 | 31.9406 | 313.9 | 451.61 |
|   | 302 | 31.7094 |   |   |
| Comparison 2 | 340 | 72.3600 | 228.7 | 225.25 |
|   | 298 | 61.1000 |   |   |
| Comparison 3 | 340 | 50.0762 | 255.7 | 323.44 |
|   | 300 | 45.1762 |   |   |

Comparison 1: Tinuvin 384-2 ® (Ciba)

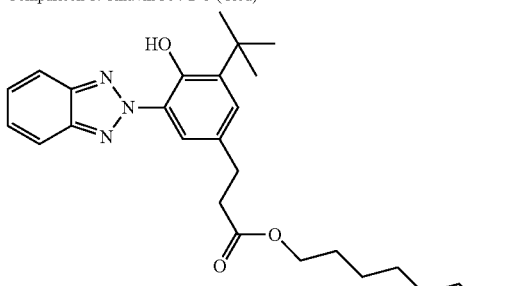

Comparison 2: Tinuvin P ® (Ciba)

TABLE 1-continued

| Example number | Peak position (nm) | Extinction coefficient [l/cm * g] | T-onset (°C.) | Molar mass (g/mol) |
| --- | --- | --- | --- | --- |

Comparison 3: Tinuvin 329 ® (Ciba)

The invention claimed is:

1. A method of stabilizing an inanimate organic material, comprising combining the inanimate organic material with a UV absorber or stabilizer, which comprises:

a benzotriazole of formula (I)

$$[B\!\!-\!\!]_n\!\!-\!\!A \quad (I)$$

wherein B is an optionally substituted 2-(2-hydroxyphenyl)-2H-benzotriazole group, n is an integer from 3 to 20, and A is an n-valent organic radical.

2. The method of claim 1, wherein the benzotriazole is of formula (Ia)

(Ia)

n is an integer from 3 to 20, $R^1$ is H, $C_1$-$C_{20}$-alkyl, arylalkyl, $C_5$-$C_{20}$-alkoxycarbonylalkyl, or $C_3$-$C_{15}$-cycloalkyl, $R^3$ is H, halogen, $CF_3$, or $COOR^4$, $R^4$ is H or $C_1$-$C_{20}$-alkyl, $R^2$ is a single bond, O, $NR^7$ or a group of formula (IIa)

(IIa)

(*bonding to benzotriazole
**bonding to A)

m is an integer from 0 to 4, p is 0 or 1, $R^5$ is H or $C_1$-$C_{20}$-alkyl, $R^6$ is H or $C_1$-$C_{20}$-alkyl, X is O or $NR^7$, and $R^7$ is H or $C_1$-$C_{20}$-alkyl.

3. The method of claim 1, wherein the benzotriazole is of formula (Ib)

(Ib)

$R^{11}$ is H, arylalkyl, $C_5$-$C_{20}$-alkoxycarbonylalkyl, or $C_3$-$C_{15}$-cycloalkyl, $R^{11}$ is H, halogen, $CF_3$, or $COOR^{14}$, $R^{14}$ is H or $C_1$-$C_{20}$-alkyl, $R^{12}$ is a single bond, O, $NR^7$, or a group of formula (IIa)

(IIa)

(*bonding to benzotriazole
**bonding to A)

m is an integer from 0 to 4, p is 0 or 1, $R^5$ is H or $C_1$-$C_{20}$-alkyl, $R^6$ is H or $C_1$-$C_m$-alkyl, X is O or $NR^7$, and $R^7$ is H or $C_1$-$C_{20}$-alkyl.

4. The method of claim 1,
wherein the benzotriazole is of formula (Ic)

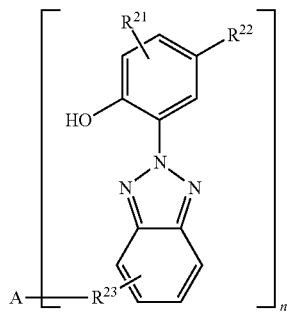
(Ic)

wherein $R^{21}$ is H, $C_1$-$C_{20}$-alkyl, arylalkyl, $C_5$-$C_{20}$-alkoxy-carbonylalkyl, or $C_3$-$C_{15}$-cycloalkyl,
$R^{22}$ is H, $C_1$-$C_{20}$-alkyl, or $COOR^{24}$,
$R^{24}$ is H or $C_1$-$C_{20}$-alkyl,
$R^{23}$ is a single bond, O, $NR^7$, or a group of formula (IIa)

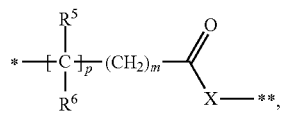
(IIa)

(*bonding to benzotriazole
**bonding to A)

m is an integer from 0 to 4,
p is 0 or 1,
$R^5$ is H or $C_1$-$C_{20}$-alkyl,
$R^6$ is H or $C_1$-$C_{20}$-alkyl,
X is O or $NR^7$, and
$R^7$ is H or $C_1$-$C_{20}$-alkyl.

5. The method of claim 1, wherein the molecular weight of the benzotriazole of formula (I) is from 1100 g/mol to 5000 g/mol.

6. The method of claim 1,
wherein A is an n valent organic radical of formula (III):

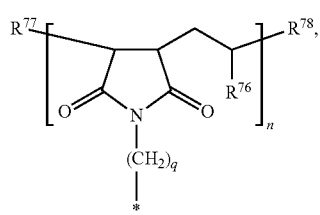
(III)

n is an integer from 3 to 20,
q is an integer from 0 to 10,
$R^{76}$ is H, aryl, or $C_1$-$C_{30}$-alkyl,
$R^{77}$ is H, $C_1$-$C_{20}$-alkyl, or $C_1$-$C_{20}$-alkoxy,
$R^{78}$ is H, $C_1$-$C_{20}$-alkyl, or $C_1$-$C_{20}$-alkoxy, and
* designates the bonding of the benzotriazole to the n-valent organic radical of formula (III).

7. The method of claim 1,
wherein A is an n-valent organic radical of formula (IIIa)

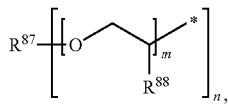
(IIIa)

n is an integer from 3 to 20,
each m is independently an integer from 0 to 10,
$R^{87}$ is a linear or branched $C_1$-$C_{20}$-alkane in which n hydrogens are replaced by a bond,
$R^{88}$ is H or linear or branched $C_1$-$C_{20}$-alkyl, and
* designates the bonding of the benzotriazole to the n-valent organic radical of formula (Ma).

8. The method of claim 1,
wherein A is an n-valent organic radical of formula (IIIb)

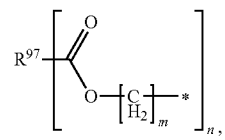
(IIIb)

n is an integer from 3 to 20,
each m is independently an integer from 0 to 10,
$R^{97}$ is a linear or branched $C_1$-$C_{20}$-alkane in which n hydrogens are replaced by a bond, and
* designates the bonding of the benzotriazole to the n-valent organic radical of formula (Mb).

9. The method of claim 1,
wherein A is a trivalent organic radical of formula (IIIc)

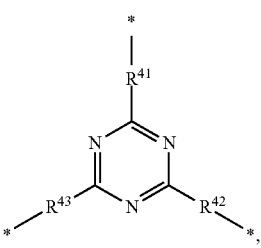
(IIIc)

$R^{41}$, $R^{42}$, $R^{43}$ are each independently a $C_1$-$C_{20}$-alkylene, and
* designates the bonding of the benzotriazole to the trivalent organic radical of formula (IIIc).

10. The method of claim 1,
wherein A is a trivalent organic radical of formula (IIId)

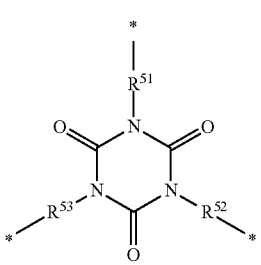
(IIId)

$R^{51}, R^{52}, R^{53}$ are each independently a $C_1$-$C_{20}$-alkylene, and

* designates the bonding of the benzotriazole to the trivalent organic radical of formula (IIId).

11. The method of claim 1,
wherein A is a tetravalent organic radical of formula (IIIe)

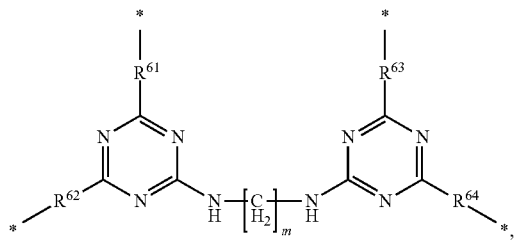

(IIIe)

m is an integer from 0 to 10,
$R^{61}, R^{62}, R^{63}, R^{64}$ are each independently a $C_1$-$C_{20}$-alkylene, and

* designates the bonding of the benzotriazole to the tetravalent organic radical of formula (IIIe).

12. A method of stabilizing a plastic, comprising combining the plastic with a photoprotective agent or stabilizer, comprising a benzotriazole of formula (I)

$$[B\!\!-\!\!]_n\!\!-\!\!A \qquad (I)$$

wherein B is an optionally substituted 2-(2-hydroxyphenyl)-2H-benzotriazole group,
n is an integer from 3 to 20, and
A is an n-valent organic radical.

13. A method of stabilizing a plastic against an effect of light, comprising combining the plastic with the benzotriazole of formula (I)

$$[B\!\!-\!\!]_n\!\!-\!\!A \qquad (I)$$

wherein B is an optionally substituted 2-(2-hydroxyphenyl)-2H-benzotriazole group,
n is an integer from 3 to 20, and
A is an n-valent organic radical.

14. An inanimate organic material stabilized against the effect of light, oxygen and heat by the method of claim 1,
wherein the comprising 0.01 to 10% by weight, based on the amount of the inanimate organic material, of the benzotriazole.

15. The method of claim 7, wherein n is an integer from 5 to 20.

16. The method of claim 1, wherein the inanimate organic material is a plastic or a wax.

17. The method of claim 1, wherein the inanimate organic material is a plastic molding.

18. The method of claim 1, wherein the inanimate organic material is a textile.

19. The method of claim 1, wherein the inanimate organic material is a cosmetic preparation.

20. The method of claim 13, wherein the plastic is stabilized against an effect of oxygen on the plastic.

* * * * *